United States Patent
Petrat et al.

(10) Patent No.: US 8,604,227 B2
(45) Date of Patent: Dec. 10, 2013

(54) PROCESS FOR PREPARING LINEAR ALPHA,OMEGA-DICARBOXYLIC DIESTERS

(75) Inventors: Frank-Martin Petrat, Muenster (DE); Franz-Erich Baumann, Duelmen (DE); Harald Haeger, Luedinghausen (DE); Guido Walther, Rostock (DE); Andreas Martin, Berlin (DE); Angela Koeckritz, Berlin (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/634,111

(22) PCT Filed: Nov. 19, 2010

(86) PCT No.: PCT/EP2010/067800
§ 371 (c)(1),
(2), (4) Date: Sep. 11, 2012

(87) PCT Pub. No.: WO2011/110249
PCT Pub. Date: Sep. 15, 2011

(65) Prior Publication Data
US 2013/0006005 A1    Jan. 3, 2013

(30) Foreign Application Priority Data

Mar. 12, 2010  (DE) .................. 10 2010 002 809

(51) Int. Cl.
*C07C 51/10*  (2006.01)
(52) U.S. Cl.
USPC ........................................ 554/129
(58) Field of Classification Search
USPC ........................................ 554/129
See application file for complete search history.

(56) References Cited

U.S. PATENT DOCUMENTS

| | | |
|---|---|---|
| 2010/0312012 A1 | 12/2010 | Hannen et al. |
| 2011/0015434 A1 | 1/2011 | Hannen et al. |
| 2012/0245375 A1 | 9/2012 | Hannen et al. |

FOREIGN PATENT DOCUMENTS

WO    2011 160730    12/2011

OTHER PUBLICATIONS

Zhu et al. : "Preparation of terminal oxygenates from renewable naturals oils by one-pot metathesis-isomerisation-methoxycarbonylatio-transesterification reaction sequence", Green Chemistry, vol. 8, 2006, pp. 746-749.*
U.S. Appl. No. 13/806,555, filed Dec. 21, 2012, Hannen, et al.
Zhu, Y., et al., "Preparation of terminal oxygenates from renewable natural oils by a one-pot metathesis-isomerisation-methoxycarbonylation-transesterification reaction sequence," Green Chemistry, vol. 8, pp. 746 to 749, (Jul. 7, 2006), XP-002618353.
Jimenez-Rodriguez, C., et al., "Dicarboxylic acid esters from the carbonylation of unsaturated esters under mild conditions," Inorganic Chemistry Communications, vol. 8, No. 10, pp. 878 to 881, (Oct. 1, 2005), XP-5077103.
International Search Report Issued Feb. 7, 2011 in PCT/EP10/67800 Filed Nov. 19, 2010.

* cited by examiner

*Primary Examiner* — Deborah D Carr
(74) *Attorney, Agent, or Firm* — Oblon, Spivak, McClelland, Maier & Neustadt, L.L.P.

(57) ABSTRACT

The invention provides a process for preparing linear alpha, omega-dicarboxylic diesters by reacting a triglyceride containing fatty acid residues having monounsaturated or polyunsaturated carbon chains with carbon monoxide, an acid and an OH-group donor in one reaction step in the presence of a catalyst.

20 Claims, No Drawings

PROCESS FOR PREPARING LINEAR ALPHA,OMEGA-DICARBOXYLIC DIESTERS

The invention relates to a process for preparing linear alpha,omega-dicarboxylic diesters, in particular linear alpha, omega-dicarboxylic dialkyl esters, by converting triglycerides in one reaction step.

Alpha,omega-dicarboxylic acids and their esters are important industrial chemicals, which are used for example in the synthesis of polyesters and polyamides. Furthermore, they are also used as lubricants and plasticizers for plastics.

In the prior art, dicarboxylic diesters and also monocarboxylic esters with chain lengths of 3 to 20 carbon atoms are prepared by catalytic alkoxycarbonylation of olefins or olefinically unsaturated monocarboxylic esters in the presence of carbon monoxide, a source of OH groups and an acid.

Processes of this type are described for example in WO 2004/014834 A1 and WO 2005/079981 A1. Complex compounds which contain, as central atom, a metal of subgroup VIII or a compound thereof and, as ligands, phosphines such as for example bidentate phosphines are used as catalyst system for the reaction. The reaction is carried out at temperatures of −30° C. to 49° C. and under a CO partial pressure of less than $30 \times 10^5$ Nm$^{-2}$. The reaction process can be configured to be discontinuous or continuous, as described for example in WO 2007/020379 A1.

Some prior art processes additionally describe the presence of booster components in the catalyst system, such as, for example, phenols (WO2009/010782 A1) or heteropoly acids (U.S. Pat. No. 4,386,217, JP 62161737). It is also possible to use additional solvents, as described for example in WO 01/68583 A1.

The hydroxycarbonylation of unsaturated $C_4$-$C_{20}$-carboxylic acids directly to give dicarboxylic acids has been described in WO 2004/103942 A1.

The scientific literature from Cole-Hamilton et al. (Inorg. Chem. Commun. 8 (2005) 878) reports on the isomerizing methoxycarbonylation of unsaturated fatty acid methyl esters having 3 to 18 carbon atoms in the chain with the catalyst system Pd/bis(di-tert-butylphosphinomethyl)benzene as catalyst in methanol and in the presence of methanesulfonic acid under mild conditions. This publication also reports that 1,19-nonadecanedicarboxylic dimethyl ester can be obtained by means of catalytic alkoxycarbonylation from methyl oleate, methyl linoleate or methyl linolenate. The catalyst used for the reaction was a palladium complex of bis(di-tert-butylphosphinomethyl)benzene (DTBPMB). Furthermore, methanesulfonic acid and methanol were used in the reaction.

Monocarboxylic esters were the product of the reaction of olefins without further functional groups (D. J. Cole-Hamilton et al., Chem. Commun. (2004) 1720). Using similar catalyst systems it is possible to convert short-chain olefins, such as, for example, ethylene, into carboxylic esters (WO98/41495 A1, WO96/19434 A1, WO99/21820 A1). Conjugated dienes produce mono- and dicarboxylic acids (WO2004/103948 A1, WO2006/084892 A1, WO2006/084889 A1, WO2008/075108 A1) and unsaturated nitriles produce cyanocarboxylic acids or esters thereof (WO01/72697 A1). Both 5-cyanovaleric acid, adipic acid and adipic esters have been synthesized from corresponding pentenoic acid derivatives (WO02/48094 A1, WO02/46143 A1, US2003/0105348). Methyl butyrates have been prepared from propylene (U.S. Pat. No. 3,793,369). In U.S. Pat. No. 3,906,015 phosphinites, phosphonites, thiophosphinites and -phosphonites were used as ligands for Pd catalysts in the alkoxycarbonylation of olefins. Pd catalysts in combination with copper salts and alkali metal halides have been used for preparing carboxylic esters from olefins, CO, $O_2$ and alcohols, although the linear esters are not preferentially produced using this system (JP61-275246).

Other catalyst systems for preparing carboxylic alkyl esters contain cobalt as active metal, pyridines or quinolines as additives, reaction temperatures of 100-180° C. are required, and only unsubstituted olefins are mentioned as substrates (U.S. Pat. No. 3,507,891, U.S. Pat. No. 3,976,670, SU952838, JP53-015310). For the preparation of isobutyrate from propylene, a combination of Cu(I) catalysts (EP 0 105 699 A1) or Cu(I) and Ag compounds (JP58-201748) and the expensive $BF_3$ has been described as catalyst system.

For linear $C_2$-$C_{12}$-olefins and cyclohexene, trifluoromethanesulfonic acid has been used as catalyst in the reaction with CO and $H_2O$ or alcohols to give dicarboxylic acids or esters thereof (U.S. Pat. No. 3,965,132).

Further methods of the prior art for preparing alpha,omega-dicarboxylic acids or alpha,omega-dicarboxylic esters were metathesis reactions or enzymatic reactions. Here, the products were prepared by oxidation of long-chain carboxylic acids, for example a cytochrome-P-450 oxidation of an omega-hydroxycarboxylic acid. One example of the metathesis reaction is the metathesis of methyl oleate, via which a $C_{18}$-diester can be prepared. However, these processes have the disadvantage that they only proceed as far as a reaction equilibrium and thus permit a conversion of only about 50% of the starting material. Furthermore, large amounts of by-products are produced, such as, for example, 9-octadecene in the present case.

The publication of Cole-Hamilton in Inorganic Chem. 8 (2005) 878 to 881 is one of the first publications in which it is shown that an alpha,omega-dicarboxylic dialkyl ester such as 1,19-nonadecanedicarboxylic dimethyl ester can be prepared selectively and with a high yield from fatty acid monomethyl esters, such as for example methyl oleate. However, the process described in this publication has the disadvantage that triglycerides cannot be used directly, but only the corresponding fatty acid monomethyl esters.

The reaction therefore firstly requires a transesterification of the fatty acid glycerol esters to the corresponding fatty acid monomethyl esters before the catalytic alkoxycarbonylation can take place. Consequently, the process according to the prior art requires two reaction steps for the preparation of alpha,omega-dicarboxylic esters. The prior art therefore discloses only processes for preparing linear alpha,omega-dicarboxylic diesters, in which, firstly, the corresponding fatty acid esters are prepared from the triglyceride by transesterification, and then a catalytic alkoxycarbonylation is carried out.

It is therefore the technical object of the invention to provide a process for preparing linear alpha,omega-dicarboxylic diesters which makes it possible to cost-effectively prepare the reaction product directly from triglycerides in just one reaction step.

Hitherto, no catalytic process is known from the prior art in which linear alpha,omega-dicarboxylic dialkyl esters can be prepared directly from triglycerides in one reaction step.

The technical object of the invention is achieved by a process for preparing linear alpha,omega-dicarboxylic diesters, preferably alpha,omega-dicarboxylic dialkyl esters, where a triglyceride which contains fatty acid radicals having mono- or polyunsaturated carbon chains is reacted in the presence of a catalyst with carbon monoxide, an acid and an OH group donor, and where the reaction is carried out in one reaction step.

The advantage of this process compared with the prior art is the saving of one reaction step and, associated therewith, an essential simplification of the technical course of such a process. Furthermore, as a result of simplifying the process, it can also be carried out more cost-effectively.

A further advantage of the process according to the invention is also that the catalyst can be used in smaller amounts than known in the prior art. Even at relatively small use amounts of the catalyst, high yields and selectivities are achieved.

Furthermore, smaller amounts of solvents are also required in the reaction, which likewise simplifies the reaction process.

It has been found that overall in the single-stage process according to the invention, an increase in the total yield of dicarboxylic diester was recorded compared with the two-stage process.

For the person skilled in the art it was not to be expected that the catalytic alkoxycarbonylation described in the prior art cannot only be carried out with fatty acid monoalkyl esters as starting materials, but also with high yields and high selectivity from corresponding triglycerides which contain fatty acid radicals having mono- or polyunsaturated carbon chains. It was surprising that these triglycerides are comparable, in respect of their reactivity within this catalytic reaction system, with the reaction behavior of the fatty acid monoalkyl esters which are used in the prior art as starting material for the reaction.

Consequently, with the process according to the invention, the alpha,omega-dicarboxylic diesters are directly accessible in a simple manner from triglycerides which are preferably used as plant oils. The hitherto required transesterification of the fatty acid glycerol esters to give the corresponding fatty acid alkyl esters is not necessary.

By means of the process according to the invention linear alpha,omega-dicarboxylic diesters of a carbon chain length of from $C_{12}$ to $C_{23}$, preferably $C_{16}$ to $C_{20}$ and particularly preferably $C_{18}$ and $C_{19}$ are prepared.

Preferably, the triglycerides which contain fatty acid radicals having mono- or polyunsaturated carbons used are plant oils having mono- or polyunsaturated fatty acid radicals. Particular preference is given to using triglycerides selected from the group sunflower oil, high oleic sunflower oil, rapeseed oil, high oleic or high erucic acid rapeseed oil, olive oil, castor oil, sesame oil, soya oil, corn oil, palm oil, linseed oil, walnut oil, wheatgerm oil, grapeseed oil, evening primrose oil, safflower oil, peanut oil, hemp oil, jojoba oil, tung oil, cottonseed oil and jatropha oil or mixtures thereof.

As plant oils, particular preference is given to using high oleic sunflower oil (HO sunflower oil) or high oleic or high erucic acid rapeseed oil. In a preferred embodiment, the triglycerides comprise at least 50% by weight, preferably at least 70% by weight and particularly preferably at least 90% by weight of mono- or polyunsaturated fatty acid radicals. High oleic sunflower oil comprises a fraction of fatty acids of at least 80% by weight. High oleic rapeseed oil comprises a fatty acid fraction of at least 50% by weight. High erucic acid rapeseed oil comprises a fatty acid fraction of at least 50% by weight.

The catalyst used is preferably a catalyst which comprises an element of group VIIIb. The catalyst is preferably a complex compound which comprises compounds from the group of the phosphorus(III) compounds as ligands. The catalysts used preferably comprise palladium and ligands of trivalent phosphorus. The ligands used are particularly preferably phosphines, phosphinites or phosphonites. These ligands can be mono- or bidentate ligands, at least one ligand from the group of phosphines being present. Particularly preferred ligands are bis(di-tert-butylphosphinomethyl)benzene and also the ligands listed below:

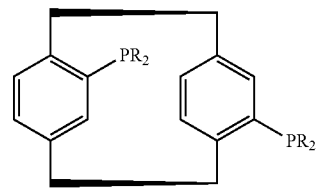

Bisphosphine with
paracyclophane backbone
(PHANEPHOS and analogs)
R = alkyl (in particular tert-butyl,
cyclohexyl), aryl (in particular phenyl)

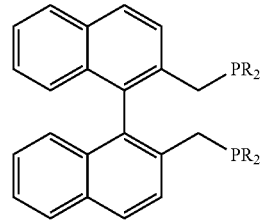

NAPHOS and analogs
R = alkyl (in particular
tert-butyl, cyclohexyl),
aryl (in particular phenyl)

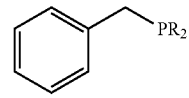

Benzyldialkyl- and benzyldiaryl
phosphines R = alkyl
(in particular tert-butyl,
cyclohexyl), aryl
(in particular phenyl)

The palladium is used in the form of precursor compounds, such as, for example, palladium salts or other palladium complex compounds in which two weakly coordinated ligands can be readily replaced by the ligands of the trivalent phosphorus. This takes place in a possible pre-reaction of the catalyst or directly upon combining the palladium component and the P(III) component in situ.

Examples of palladium compounds which can thus be used are palladium acetate, palladium acetylacetonate and palladium nitrate.

The OH group donors used are preferably linear and branched aliphatic alcohols having 1 to 10 carbon atoms or water, and also mixtures thereof. Particularly preferred alcohols are methanol, ethanol, propanol and butanol. These alcohols can be used both as OH group donors and as solvents in the reaction. Particular preference is given to using methanol.

Furthermore, inert aprotic solvents can additionally be used. Examples of these compounds are anisoles, diethyl ether, methyl tert-butyl ether, methyl pentanoate, diphenyl ether, dimethyl adipate, tetrahydrofuran, dioxane, methyl nonanoate, toluene.

As acid, preference is given to using acids with a pKa value measured at 25° C. of less than 3. These are usually medium-strength to strong acids. They are preferably selected from the group organic sulfonic acids, phosphoric acids, halogenated carboxylic acids, phosphonic acids, sulfuric acid, nitric acid, perchloric acid, halohydric acid, polymer substituted with sulfonic acid groups, or mixtures thereof.

A polymer substituted with sulfonic acid groups is, for example, Nafion, which is a sulfonated tetrafluoroethylene polymer.

The process according to the invention is preferably carried out as reaction by means of homogeneous catalysis in the liquid phase. For this, firstly the triglyceride is combined with the catalyst and the OH group donor in the presence of the acid and then reacted at elevated temperature and while introducing carbon monoxide. This then directly gives the reaction product as alpha,omega-dicarboxylic diester. This can optionally be further purified, for example by filtration and recrystallization.

In a particularly preferred embodiment, the catalyst is added, based on triglyceride, in amounts of from 0.05 to 15 mol %, preferably from 0.5 to 5 mol %.

It is also preferred to establish the ratio of palladium to P(III) groups in the catalyst in the range from 1:2 to 1:12 mol/mol.

The triglyceride is preferably used in the ratio to the OH group donor during the reaction in the ratio greater than or equal to 1:30 mol/mol.

Preferably, the molar ratio of the added acid to the triglyceride is 0.1:1 to 0.6:1.

The process according to the invention is preferably carried out at a reaction temperature of from 0 to 130° C., preferably from 60 to 90° C.

The CO partial pressure during the reaction is preferably 1000 to 60 000 hPa, preferably 10 000 to 30 000 hPa.

By means of the process according to the invention it is possible to prepare linear alpha,omega-dicarboxylic diesters in one reaction step in a simple and cost-effective manner. Starting materials which can be used directly are cost-effective plant oils having mono- or polyunsaturated fatty acid radicals. The reaction can be carried out in high yields and with high selectivity, meaning that further work-up with the removal of by-products can be avoided.

The reaction process according to the invention is thus a cost-effective alternative to the preparation processes of alpha,omega-dicarboxylic diesters hitherto available in the prior art.

The examples below are intended to illustrate the invention in more detail.

EXAMPLES

Example 1

A volume of 40 ml of triglyceride, here sunflower oil, is reacted with 2.3 mol % of catalyst, in this example Pd/bis(di-tert-butylphosphinomethyl)benzene, in methanol (molar ratio of sunflower oil to OH group donor ca. 1:72) and in the presence of 45 mol % of methanesulfonic acid at a temperature of 80° C. and a CO partial pressure of 30 000 hPa in a reaction time of 32 hours with constant stirring to give the alpha,omega-dicarboxylic diester, here 1,19-nonadecanedicarboxylic dimethyl ester. For the anaerobic preforming of the catalyst, a five-fold ligand excess is used.

For the purification of the 1,19-nonadecanedicarboxylic dimethyl ester, the reaction product separated from the catalyst by filtration at greater than or equal to 40° C. is recrystallized in methanol, and washed in ice-cold methanol (less than or equal to −5° C.) and filtered.

The molar amount of the 1,19-nonadecanedicarboxylic dimethyl ester prepared in this way is equivalent to the consumed molar amount of carbon monoxide, which can be determined from the pressure loss of the CO partial pressure during the reaction. The yield is above 85% based on the triglyceride.

Example 2

Comparative Example 880 ml of sunflower oil and 248 ml of THF are added to a 2 l round-bottomed flask. With constant stirring, 8.0 g of NaOH dissolved in 220 ml of $CH_3OH$ are added dropwise at room temperature. The mixture is stirred for a further 4 hours once the metered addition is complete. The solvents are then drawn off on a rotary evaporator and the glycerol is removed by freezing out and separating off via a chilled suction filter. The yield of crude methyl oleate is 99%.

210 ml of crude methyl oleate are reacted with 2.4 mol % of catalyst, in this example Pd/bis(di-tert-butylphosphinomethyl)benzene, in 770 ml of methanol and in the presence of 45 mol % of methanesulfonic acid at a temperature of 80° C. and a CO partial pressure of 30 000 hPa in a reaction time of 22 hours with constant stirring to give the alpha,omega-dicarboxylic diester, here 1,19-nonadecanedicarboxylic dimethyl ester. The catalyst was preformed in the same way as under example 1. The crude diester is purified as described under example 1. The yield is 76%, based on methyl oleate.

Examples 3-14

308.8 μmol (0.3 ml) of triglyceride, here sunflower oil, and 14.4 μmol (1.38 mg) of methanesulfonic acid are subjected to the reaction described in example 1 at the same reaction temperature (80° C.) and for the same reaction time (32 h) in each case.

Table 1 lists the yields based on the triglyceride and selectivities of experiments with different catalyst concentrations, solvent concentrations and different CO partial pressures.

TABLE 1

| Ex. | Concentration c(catalyst) [mol %] | Ratio v(MeOH)/ v(starting material) [ml/ml] | Pressure P(CO) [hPa] | 1,19-nonadecane-dicarboxylic dimethyl ester Yield [%] | Selectivity [%] |
|---|---|---|---|---|---|
| 3 | 4.8 | 4 | 30000 | 97 | 94 |
| 4 | 2.4 | 4 | 30000 | 85 | 89 |
| 5 | 4.8 | 3 | 30000 | 90 | 94 |
| 6 | 4.8 | 4 | 20000 | 85 | 94 |
| 7 | 2.4 | 4 | 20000 | 85 | 93 |
| 8 | 1.2 | 4 | 20000 | 72 | 81 |
| 9 | 4.8 | 3 | 20000 | 94 | 94 |
| 10 | 2.4 | 3 | 20000 | 78 | 92 |
| 11 | 4.8 | 4 | 10000 | 94 | 94 |
| 12 | 2.4 | 4 | 10000 | 95 | 92 |
| 13 | 4.8 | 3 | 10000 | 92 | 94 |
| 14 | 2.4 | 3 | 10000 | 87 | 87 |

The table shows that high yields and selectivities are achieved even in the case of small amounts of catalyst. For example, catalyst amounts of just 1.2 mol % suffice to achieve similar yields to comparative example 2 which shows the 2-stage prior art process and uses six-times the amount of catalyst based on methyl oleate or a fatty acid radical in the triglyceride. At catalyst amounts of just 2.4 mol % yields are achieved which are far above the yields of comparative example 2.

The invention claimed is:
1. A process for preparing a linear alpha, omega-dicarboxylic diester, the process comprising reacting a triglyceride comprising fatty acid radicals having mono- or polyunsaturated carbon chains, in the presence of a catalyst, with carbon monoxide, an acid and an OH group donor to form a linear alpha, omega-dicarboxylic diester, such that the reacting occurs in one reaction step.

2. The process of claim 1, wherein the triglyceride is at least one plant oil having mono- or polyunsaturated fatty acid radicals.

3. The process of claim 1, wherein the triglyceride is selected from the group consisting of sunflower oil, high oleic sunflower oil, a rapeseed oil, live oil, castor oil, sesame oil, soya oil, corn oil, palm oil, linseed oil, walnut oil, wheatgerm oil, grapeseed oil, evening primrose oil, safflower oil, peanut oil, hemp oil, jojoba oil, tung oil, cottonseed oil, jatropha oil, and mixtures thereof.

4. The process of in claim 1, wherein the catalyst comprises an element of group VIIIb.

5. The process of claim 1, wherein the catalyst comprises a ligand
comprising phosphorus(III).

6. The process of claim 1, wherein the catalyst comprises Pd and at least one ligand selected from the group consisting of a phosphine, a phosphinite, and a phophonite.

7. The process of claim 1, wherein the linear alpha,omega-dicarboxylic diester has a carbon chain length of $C_{12}$ to $C_{23}$.

8. The process of claim 1, wherein the OH group donor is selected from the group consisting of a linear alcohol having 1 to 10 carbon atoms, a branched alcohol having 1 to 10 carbon atoms, water, and mixtures thereof.

9. The process of claim 1, wherein the acid has a pKa value (measured at 25° C.) of less than 3.

10. The process of claim 1, wherein the acid is at least one selected from the group consisting of an organic sulfonic acid, a phosphonic acid, a halogenated carboxylic acid, phosphoric acid, sulfuric acid, nitric acid, perchloric acid, hydrohalic acid, a polymer substituted with at least one sulfonic acid group, and mixtures thereof.

11. The process of claim 1, wherein the reacting occurs in the presence of a homogeneous catalyst in the liquid phase.

12. The process of claim 1, wherein an amount of the catalyst is from 0.05 to 15 mol % based on the triglyceride.

13. The process of claim 6, wherein:
the ligand comprises P(III); and
a ratio of Pd to P(III) in the catalyst is 1:2 to 1:12 mol/mol.

14. The process of claim 1, comprising reacting the triglyceride, in the presence of the catalyst, with the carbon monoxide, the acid, the OH group donor, and an aprotic solvent.

15. The process of claim 1, wherein a ratio of the triglyceride to the OH group donor is greater than or equal to 1:30 mol/mol.

16. The process of claim 1, wherein a molar ratio of the acid to the triglyceride is 0.1:1 to 0.6:1.

17. The process of claim 1, wherein the reacting occurs at a temperature of from 0 to 130° C.

18. The process of claim 1, wherein a carbon monoxide partial pressure is 1000 to 60 000 hPa.

19. The process of claim 1, wherein the linear alpha, omega-dicarboxylic diester has a carbon chain length of $C_{16}$ to $C_{20}$.

20. The process of claim 1, wherein an amount of the catalyst is from 0.5 to 3 mol % based on the triglyceride.

* * * * *